US012790637B2

(12) United States Patent
Feurhuber et al.

(10) Patent No.: US 12,790,637 B2
(45) Date of Patent: Nov. 10, 2026

(54) METHOD FOR DETERMINING THE EFFECTIVENESS OF A STERILIZATION METHOD FOR A MEDICAL PRODUCT IN A STERILIZER, DATA PROCESSING SYSTEM, COMPUTER PROGRAM PRODUCT, AND MEDICAL PRODUCT

(71) Applicant: FRESENIUS MEDICAL CARE DEUTSCHLAND GMBH, Bad Homburg (DE)

(72) Inventors: Manuel Feurhuber, Saarbrucken (DE); Ralf Neuschwander, Bexbach (DE); Thomas Taupitz, Riegelsberg (DE); Christoph Hochenauer, Bordersdorf (AT); Valentin Schwarz, Saarbruecken (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1232 days.

(21) Appl. No.: 17/617,953

(22) PCT Filed: Mar. 20, 2020

(86) PCT No.: PCT/EP2020/057872

§ 371 (c)(1),
(2) Date: Dec. 10, 2021

(87) PCT Pub. No.: WO2020/249276

PCT Pub. Date: Dec. 17, 2020

(65) Prior Publication Data

US 2022/0257820 A1 Aug. 18, 2022

Related U.S. Application Data

(63) Continuation-in-part of application No. PCT/EP2019/072505, filed on Aug. 22, 2019.

(30) Foreign Application Priority Data

Jun. 12, 2019 (DE) ..................... 10 2019 116 013.8

(51) Int. Cl.

| | |
|---|---|
| ***C12Q 1/22*** | (2006.01) |
| ***A61L 2/07*** | (2006.01) |
| ***A61L 2/206*** | (2026.01) |
| ***A61L 2/28*** | (2006.01) |
| *A61L 103/15* | (2026.01) |

(52) U.S. Cl.

CPC .................. *C12Q 1/22* (2013.01); *A61L 2/07* (2013.01); *A61L 2/206* (2013.01); *A61L 2/28* (2013.01); *A61L 2103/15* (2026.01); *A61L 2202/122* (2013.01); *A61L 2202/14* (2013.01)

(58) Field of Classification Search

CPC ... C12Q 1/22; A61L 2/07; A61L 2/206; A61L 2/28; A61L 2202/122; A61L 2202/14; A61L 2202/24

See application file for complete search history.

(56) References Cited

U.S. PATENT DOCUMENTS

2002/0095617 A1* 7/2002 Norman ................ H10F 39/107
714/10

FOREIGN PATENT DOCUMENTS

| | | | |
|---|---|---|---|
| EP | 3470085 | A1 | 4/2019 |
| WO | 0027228 | A1 | 5/2000 |
| WO | 0027229 | A1 | 5/2000 |
| WO | 2016174143 | A1 | 11/2016 |
| WO | 2020249243 | A1 | 12/2020 |

OTHER PUBLICATIONS

International Search Report and Written Opinion issued in corresponding International Patent Application No. PCT/EP2020/057872 (with English translation of International Search Report) dated Apr. 14, 2020 (11 pages).

* cited by examiner

*Primary Examiner* — David W Berke-Schlessel
*Assistant Examiner* — Susan E. Fernandez
(74) *Attorney, Agent, or Firm* — Kilyk & Bowersox, P.L.L.C.

(57) ABSTRACT

A process is presented for determining the effectiveness of sterilizing processes for medical devices with the following steps: providing a data structure, wherein the data structure represents a grid formed of a plurality of three-dimensional cells; recreating the medical device arranged in the sterilizer in the data structure in such a way that a first multiplicity of cells of the grid represent a body of the medical device and that a second multiplicity of cells represent an interior of the sterilizer which is not occupied by the body of the medical device; recreating an initial state in the data structure in such a way that each cell of the second multiplicity of cells is assigned data relating to the temperature prevailing at the location of the cell, the quantity of a first medium located in the area of the cell, and the quantity of a second medium located in the area of the cell; recreating, step by step, changes in the temperature, in the quantity of the first medium and in the quantity of the second medium occurring in each cell of the second multiplicity of cells during the sterilization process; and calculating a reduction in a germ loading achieved in each cell of the second multiplicity of cells during the sterilization process taking into consideration the prevailing temperature, quantity of the first medium and quantity of the second medium in the respective cell in each step. Furthermore, a data processing system and a computer program product for carrying out the process are presented.

13 Claims, 7 Drawing Sheets

Figure 1:
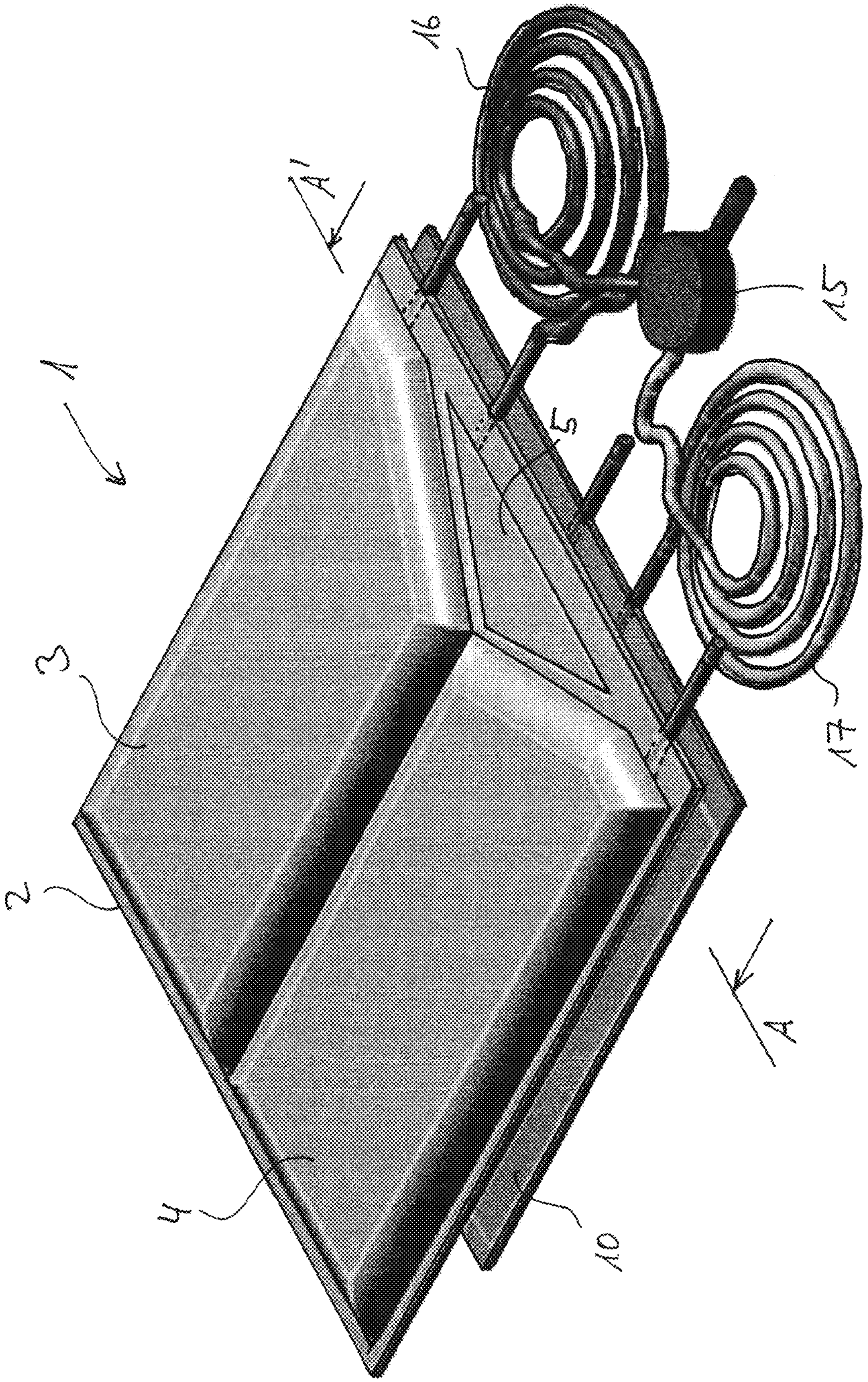

METHOD FOR DETERMINING THE EFFECTIVENESS OF A STERILIZATION METHOD FOR A MEDICAL PRODUCT IN A STERILIZER, DATA PROCESSING SYSTEM, COMPUTER PROGRAM PRODUCT, AND MEDICAL PRODUCT

This application is a National Stage Application of PCT/EP2020/057872, filed Mar. 20, 2020, which is a continuation-in-part of PCT/EP2019/072505 filed Aug. 22, 2019, and which claims priority to German Patent Application No. 10 2019 116 013.8, filed Jun. 12, 2019.

The invention relates to a process for determining an effectiveness of a sterilization process for a medical device or a packaged medicinal product in a sterilizer. In the following, for the sake of brevity, in the main medical devices are discussed, wherein packaged medicinal products are always also included in the meaning.

Sterilization processes are used in order to sterilize medical devices or packaged medicinal products before use, thus to rid them of potentially harmful germs. Known sterilization processes include steam sterilization, dry heat sterilization, autoclaving, gamma sterilization, electron-beam sterilization, ethylene oxide sterilization and plasma sterilization. Within the framework of this application, medical device also denotes medicinal products, in particular packaged medicinal products, furthermore in particular medicinal products packaged in bags, furthermore in particular solutions packaged in bags and devices for peritoneal dialysis.

The sterilization is mostly carried out in a sealed sterilization chamber of a sterilizer, into which the medical device is introduced.

In order to avoid endangering patients on whom the medical device is to be used, it must be ensured that the medical device is actually sterile, thus is substantially free of germs, after the sterilization process has been carried out.

While the fundamental effectiveness of known sterilization processes has been sufficiently proven scientifically, the actual effectiveness of a sterilization process when applied to a particular medical device is dependent on many parameters, including the shape and material properties of the medical device, and on the selected process parameters of the sterilization process, e.g. the temperature profile, quantities of media used and the process duration.

As individually checking the sterility of a medical device is impossible in practice, without in the process at least limiting the availability for use of the medical device, the sterility is proven by validating the sterilization process used. In this connection, it is scientifically proven that a sterilizing process carried out with particular parameters always achieves the desired result. Here, the desired result is defined using the factor by which a germ load in the medical device is reduced by the sterilization process. An effective sterilization can be regarded as having been effected e.g. when the germ load has been reduced by a factor of $10^{12}$.

A current process for determining the effectiveness of a sterilization process consists in introducing a sample which is provided with a known germ load at a critical point of a medical device. A critical point here denotes a point of the medical device at which a particularly small effect of the sterilization process is expected, for example because the point heats up particularly slowly, or because it is particularly difficult to reach for media used for the sterilization.

The medical device is then subjected to the sterilization process. Then, the sample is removed and the remaining germ load is determined.

Strips of paper which are inoculated with particularly temperature-stable germs, for example with *Geobacillus stearothermophilus*, are often used as samples.

If the evaluation of the sample reveals that the required reduction in the germ load has been achieved, the sterilization process is regarded as reliable and is validated.

While the described method is generally recognized, it does sometimes have considerable disadvantages. For one thing, the evaluation of the samples requires considerable effort in terms of equipment and time, since an incubation in a culture medium lasting several days is required first before an evaluation of the remaining germs, in order to arrive again at a germ density to be evaluated meaningfully. For another thing, introducing the samples into the medical device to be sterilized is often difficult. If, for example, the medical device has a sealed volume, this may have to be opened in order to introduce the sample. The results of the validation can also be distorted thereby. In addition, it can occur that a critical point of the medical device is difficult or impossible to reach for the sample, for example if the medical device comprises thin channels or tubes. A further disruptive effect exists when a sample influences the concentration of a medium used in the sterilization process, for example where a strip of paper absorbs water and thus reduces the humidity in its surroundings.

From patent applications WO 00/27228 A1 and WO 00/27229 A1, processes are known for computationally determining the reduction in a germ load achieved at a critical point of a food product during a thermal sterilization. For this purpose, however, only the temperature profile at a so-called "cold spot" of the product is simulated; the dependence on other media is not taken into consideration.

In particular in the case of sterilization processes in which more than one medium is used, these processes are inadequate.

An object of the invention is thus to provide a process for determining the effectiveness of a sterilization process for a medical device in a sterilizer which is improved with regard to the described set of problems.

A further object of the invention is to provide an improved process for validating a sterilization process for medical devices.

One or more of the named objects are achieved according to a first aspect of the invention by a process for determining the effectiveness of a sterilization process for a medical device in a sterilizer, with the following steps: providing a data structure, wherein the data structure represents a grid formed of a plurality of three-dimensional cells; recreating the medical device arranged in the sterilizer in the data structure in such a way that a first multiplicity of cells of the grid represent a body of the medical device and that a second multiplicity of cells represent an interior of the sterilizer which is not occupied by the body of the medical device; recreating an initial state in the data structure in such a way that each cell of the second multiplicity of cells is assigned data relating to the temperature prevailing at the location of the cell, the quantity of a first medium located in the area of the cell and the quantity of a second medium located in the area of the cell; recreating, step by step, changes in temperature, in the quantity of the first medium and in the quantity of the second medium occurring in each cell of the second multiplicity of cells during the sterilization process; calculating a reduction in a germ loading achieved in each cell of the second multiplicity of cells during the sterilization process taking into consideration the prevailing temperature, quantity of the first medium and quantity of the second medium in the respective cell in each step.

It has surprisingly transpired that, using processes known from computational fluid dynamics in which a continuous space is divided into discrete cells in which constant relationships are assumed in each case, not only can media flows be recreated well, but with it a current and a cumulative reduction in the germ loading can also be calculated with a high degree of accuracy for each location of the medical device, even if there is a complex geometry.

When recreating sterilization processes with more than one medium, the quantity of the individual media in each cell of the data structure is important for several reasons.

For one thing, the individual media can have a significant influence on the heat transfer between the individual cells, e.g. on the heat transfer between the interior of the sterilizer and the body of the medical device. Interior of the sterilizer here denotes the entire free interior which is not filled by solid components of the medical device. Therefore, this also includes internal cavities of the medical device.

For another thing, the quantity of the individual media can also have a direct influence on the reduction in the germ loading.

In general, the temporal profile of the germ loading N at a point of the medical device can be described with the following differential equation:

$$\frac{dN}{dt} = -k * N$$

Here, k is the so-called inactivation rate, which indicates what proportion of the germ population is deactivated or killed in an infinitesimally short time interval dt. On the one hand, the inactivation rate is heavily dependent on the temperature, wherein the inactivation rate increases approximately exponentially with the temperature. The temperature dependence of the inactivation rate can be determined using the Arrhenius equation:

$$k(T) = k_0 * e^{\frac{E}{R*T}}$$

On the other hand, the inactivation rate is also dependent on the heat transfer from the medium surrounding a germ to the germ itself. Thus, for example, at the same temperature a significantly higher inactivation rate can result if there is a high proportion of water vapour in the atmosphere than if the air is dry. Of course, the quantity or concentration of directly active media such as ethylene oxide also has a direct influence on the inactivation rate k.

Furthermore, the inactivation rate k is dependent on whether the germ loading is located in a free space or whether it is adhering to a surface. Therefore, in the following a distinction is made between a volume inactivation rate $k_V$ and a surface activation rate $k_O$. The surface deactivation rate $k_O$ is additionally dependent on a material composition of the surface.

For the computational recreation, the above-named differential equation is replaced by a finite difference equation which calculates using discrete time intervals Δt:

$$\frac{\Delta N}{\Delta t} = -k * N$$

In the finite difference equation indicated above, changes in the germ loading due to flow and diffusion are discounted; they do not play an appreciable role in conventional sterilization processes.

In the process according to the invention, it is now calculated in many individual steps how the temperature and the quantity of the individual media change in the cell of the grid. Causes for the change in the media quantities are, for example, flow and diffusion processes, but also heat transfer processes such as, for example, condensation and evaporation. In each step, the resulting change in the germ loading is then determined for each cell of the grid as well as for the boundary surfaces, with the result that, after the recreation of the complete sterilization process, the ultimately achieved reduction in the germ loading is known for every cell of the grid and for every boundary surface. The recreation therefore also relates to the edges of the cells and thus optionally the surface of the medical device. The entire sterilization process is thus computationally recreated or simulated.

The process according to the invention offers the advantage that the effectiveness of a sterilization process for a particular medical device can be determined without this process actually having to be carried out and without samples then having to be evaluated laboriously. It thereby becomes possible to determine the effects of changes on the effectiveness of the process. In the process, both design changes of the medical device and changes in the parameters of the sterilization process can be simulated. In this way, both the medical device and the sterilization process can be optimized with respect to the use of material and energy.

Furthermore, the process according to the invention offers the advantage that points of a medical device which are not accessible to samples can also be taken into consideration in the determination of the effectiveness of a sterilization process.

In a development of a process according to the invention, the quantity of a third medium in each cell can additionally be taken into consideration.

For example, ethylene oxide or hydrogen peroxide, which are used in gas or plasma sterilization, can be taken into consideration as third medium. The quantity of these media in each cell has a direct influence on the respective inactivation rate.

The reduction in the germ loading can be calculated taking into consideration a volume inactivation rate $k_V$, which is dependent on the composition of an atmosphere prevailing in the respective cell. Here, for example a proportion of water vapour in the atmosphere and/or a proportion of ethylene oxide and/or hydrogen peroxide can be taken into consideration.

In a development of a process according to the invention, for each boundary surface between a cell of the first multiplicity of cells and a cell of the second multiplicity of cells, the reduction in a germ loading on the corresponding boundary surface can be calculated, wherein for the calculation a surface inactivation rate $k_O$ is taken into consideration, which is dependent on the composition of the atmosphere prevailing in the adjacent cell of the second type and on the material of which the boundary surface consists. In this way, germ loadings of surfaces and the reduction thereof are also taken into consideration in the simulation.

According to a particular development, a phase transition of the first, second and/or third medium can be taken into consideration in the recreation of the sterilization process.

Thus, for example, before the sterilization in an autoclave a medical device can be provided with a water loading in order to provide sufficient steam for the actual sterilization procedure. For this purpose, a medical device or a gas-filled component of the medical device can be exposed to a vacuum first of all in a pre-treatment, with the result that air is suctioned out of the medical device, and then an "aeration" with steam can be effected. The steam then penetrates into the medical device and condenses on the surface of the medical device to a large extent to form water droplets.

In the actual sterilization process, these water droplets must first of all be evaporated, which has a large influence on the temperature and media distribution during the sterilization process. The recreation of the process becomes even more precise because this phase transition is taken into consideration.

According to a further embodiment of a process according to the invention, a shape change of the medical device can additionally be taken into consideration in the recreation of the sterilization process. For this purpose, values for the elastic and/or plastic behaviour of the respective material can be assigned to the cells of the grid which represent the medical device.

If, a water reserve now evaporates during the sterilization process, for example in an interior of a flexible medical device such as a blood, serum or dialysis bag, then the medical device can swell, whereby the flow and diffusion processes are significantly influenced. Taking this deformation into consideration results in an even more precise recreation of the sterilization process.

In an additional development of a process according to the invention, a diffusion of the first, second and/or third medium through the material of the medical device can be taken into consideration in the recreation of the sterilization process.

A diffusion of media can be intended or even necessary. Thus, for example, in the ethylene oxide sterilization of packaged medical devices, the ethylene oxide must diffuse through the packaging in order to reach the actual medical device. Within the meaning of the invention, the packaging here is to be understood as a component of the medical device. However, an unintended diffusion can also have an appreciable influence on the effectiveness of the sterilization process. Overall, the informative value of the recreation can be increased even further by taking the diffusion into consideration.

In a further design of a process according to the invention, a convection of the first, second and/or third medium between the cells of the second multiplicity of cells can be taken into consideration for the recreation of the sterilization process.

Convection processes are important for the distribution of media and/or energy during the sterilization process. Taking into consideration the convection therefore makes an even more precise recreation of the processes actually taking place possible.

As a rule, air is to be taken into consideration as first medium. Water, which can be present both as a liquid and as steam, is mostly to be taken into consideration as second medium. Ethylene oxide or hydrogen peroxide are possible as third medium or, in the absence of water, as second medium.

One or more of the above-named objects are achieved according to a second aspect of the invention by a process for validating a sterilization process for medical devices with the following steps: stipulating a reduction in a germ loading to be achieved by the sterilizing process; carrying out a process according to the first aspect of the invention; comparing the reduction in the germ loading determined in each cell of the second multiplicity of cells; and classifying the sterilization process as effective if the required reduction in the germ loading has been achieved for each of the cells, or classifying the sterilization process as not effective if the required reduction in the germ loading has not been achieved for at least one of the cells.

The validation of a sterilization process is greatly simplified by the described process since the introduction of samples and the subsequent evaluation of the samples can be dispensed with.

Since the validation of a sterilization process for a particular medical device is a prerequisite in many legal systems for the approval both of the sterilization process and of the medical device itself, the approval of new medical devices can be simplified and accelerated, with the result that new and innovative medical devices can be brought to market, and can thus benefit patients, more quickly.

In a further development of the process according to the invention for validating a sterilization process, a control procedure with the following steps can additionally be carried out: introducing a sample provided with a known germ loading at a predetermined point of a medical device to be sterilized, carrying out the sterilization process to be validated on the medical device, determining the reduction in the germ loading of the sample achieved by the sterilization process, and only classifying the sterilization process as effective when the reduction in the germ loading of the sample actually achieved corresponds sufficiently precisely to the reduction in the germ loading calculated for the corresponding point.

Even though the placement and subsequent evaluation of a sample is necessary for the validation according to the described further development, the process is advantageous compared with the validation according to the state of the art. Thus, for example, it can be proved by means of the simulation that the location at which the sample was introduced is actually a critical location of the medical device, thus a location at which the sterilization process brings about the smallest reduction in the germ loading. Even when the critical location of the medical device cannot be reached by a sample, it can be proved with the described process that the result of the simulation at the location at which the sample was introduced matches the actual result of the sterilization process. It can then be assumed that the simulation result is also correct for the actually critical location.

One or more of the named objects are achieved according to a third aspect of the invention by a data processing system, comprising at least one processor, a memory, input means and output means, which is developed in that program code information which, when executed by the processor, is able to prompt the latter to execute a process according to the above descriptions is stored in the memory.

The data processing system can comprise a commercially available computer, which is expediently equipped for the CPU-intensive process with one or more powerful processors and sufficient RAM.

In addition to conventional input means such as keyboard, mouse, touchscreen etc., the input means can also comprise an interface with a network, via which the data processing system is connected to a database in which information about geometric and material-specific properties of one or more medical devices is stored.

In addition to conventional output means such as monitor and/or printer, the output means can also comprise a storage medium, on which the results of the described processes are stored as data. These data can comprise tables, in which the results are represented numerically. The data can also comprise images and/or videos, by means of which the profile or the result of the described processes is visualized.

The program code information can be stored on a storage medium of the computer, for example on a hard drive, in the form of an executable computer program.

One or more of the named objects are achieved according to a fourth aspect of the invention by a computer program product, comprising a data carrier and program code information saved on the data carrier which, when executed by a processor, is able to prompt the latter to execute a process such as described previously.

One or more of the named objects are achieved according to a fifth aspect of the invention by a sterilized medical device which has been subjected to a sterilization process the effectiveness of which has been determined by a process according to the above description, or which has been validated according to a process according to the above embodiments.

One or more of the named objects are achieved according to a sixth aspect of the invention by a medical device which was produced in a sterilizer, wherein the effectiveness of the sterilization process on which this system is based has been determined by a process according to the above description, or which has been validated according to a process according to the above embodiments.

The sterilizer comprises all of the means which are necessary for carrying out the sterilization process. For example, the sterilizer also comprises the means which are necessary in order to ensure aeration with steam, but also, for example, an autoclave chamber.

The invention is explained in more detail below with reference to some exemplary representations. The embodiment examples represented are to serve only for the better understanding of the invention, without limiting it.

Figure 2:
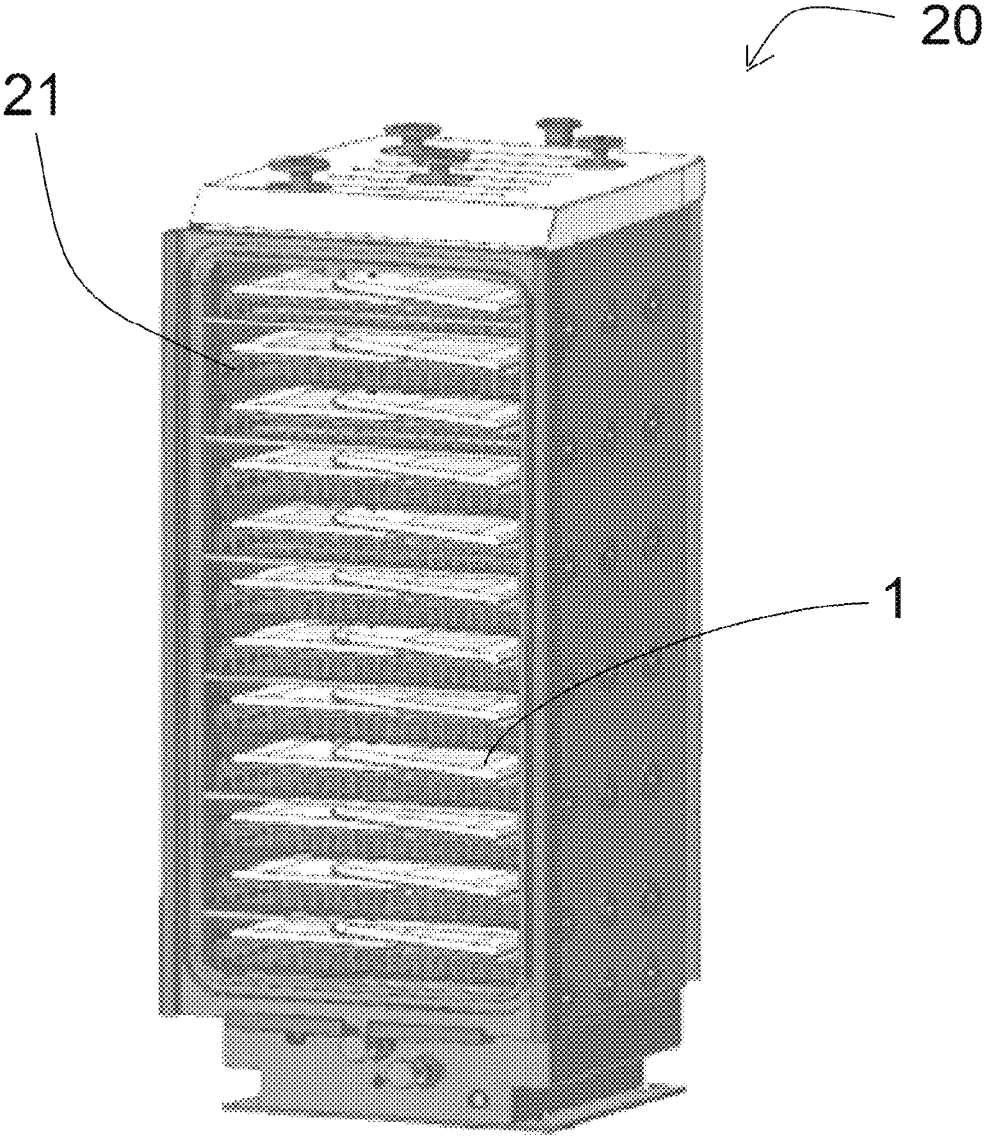
Figure 3A:
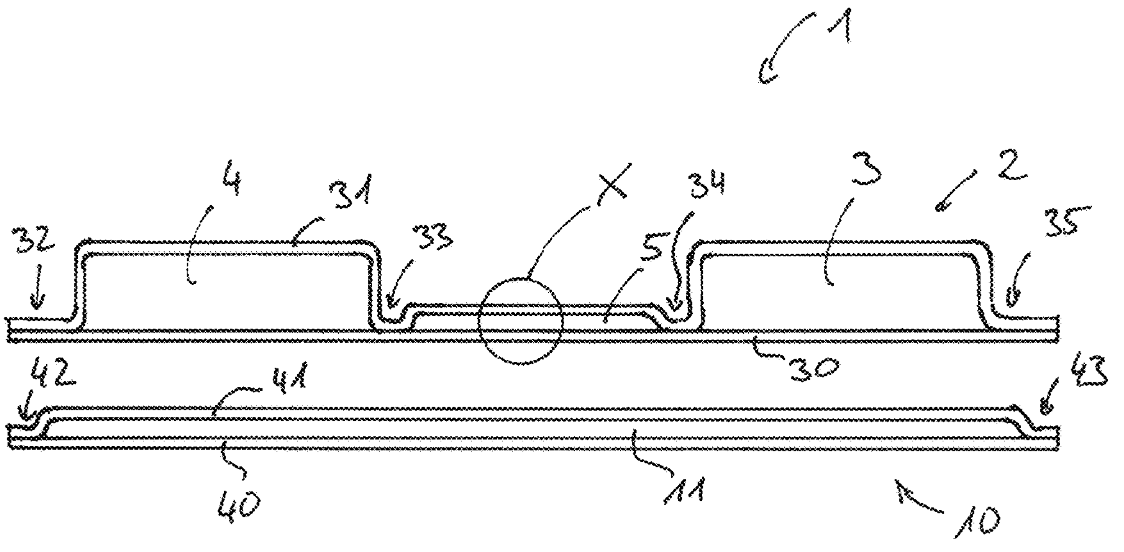
Figure 3B:
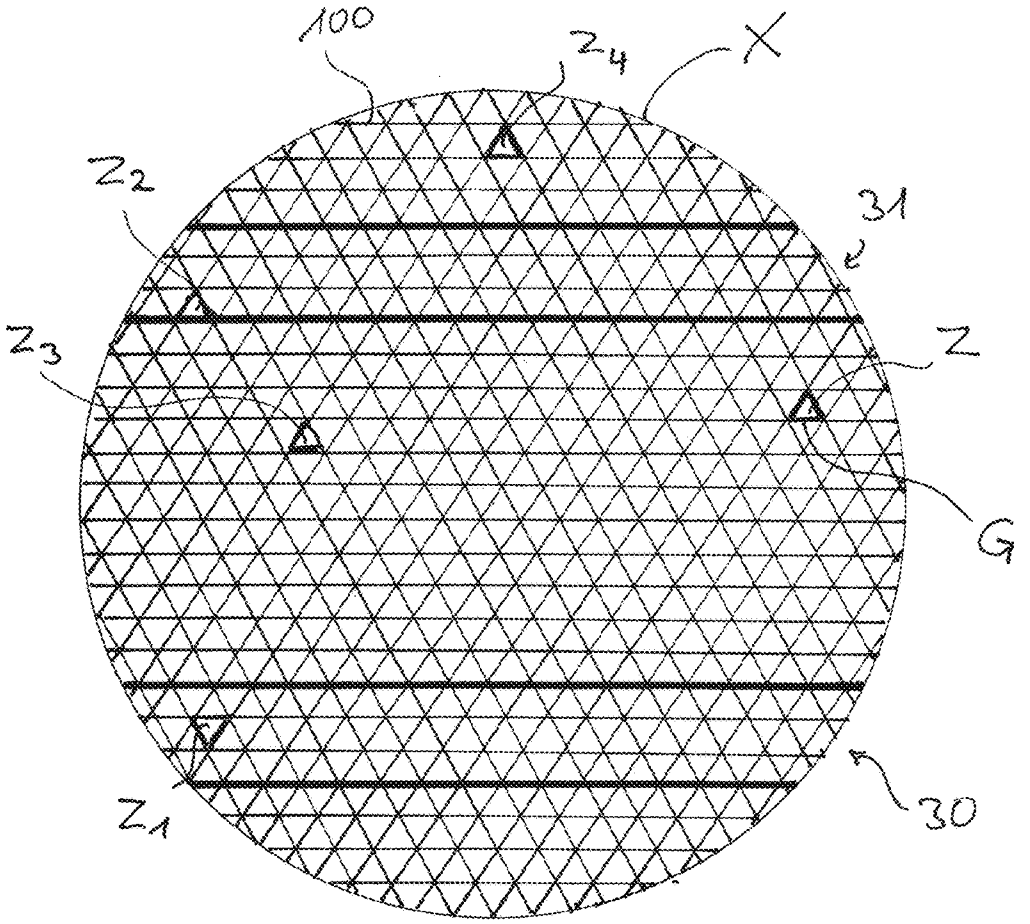
Figure 4A:
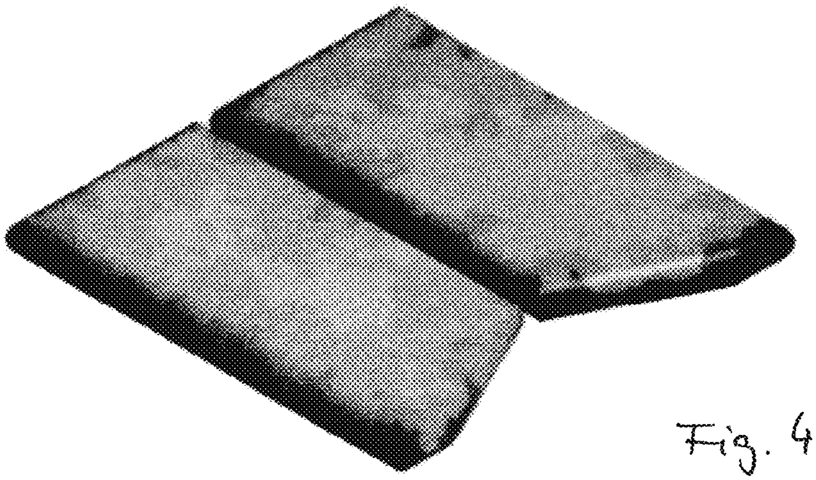
Figure 4B:
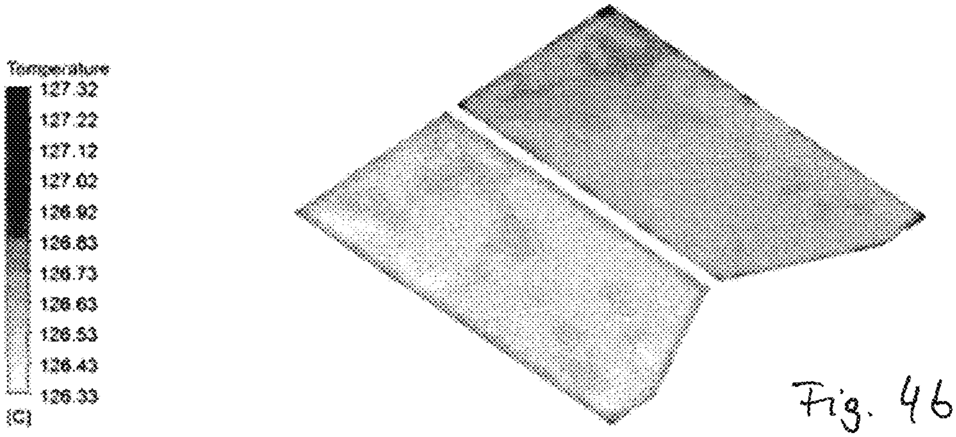
Figure 4C:
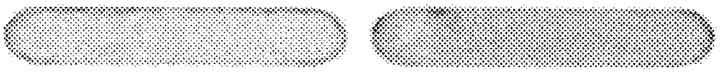
Figures 4D, 4E:
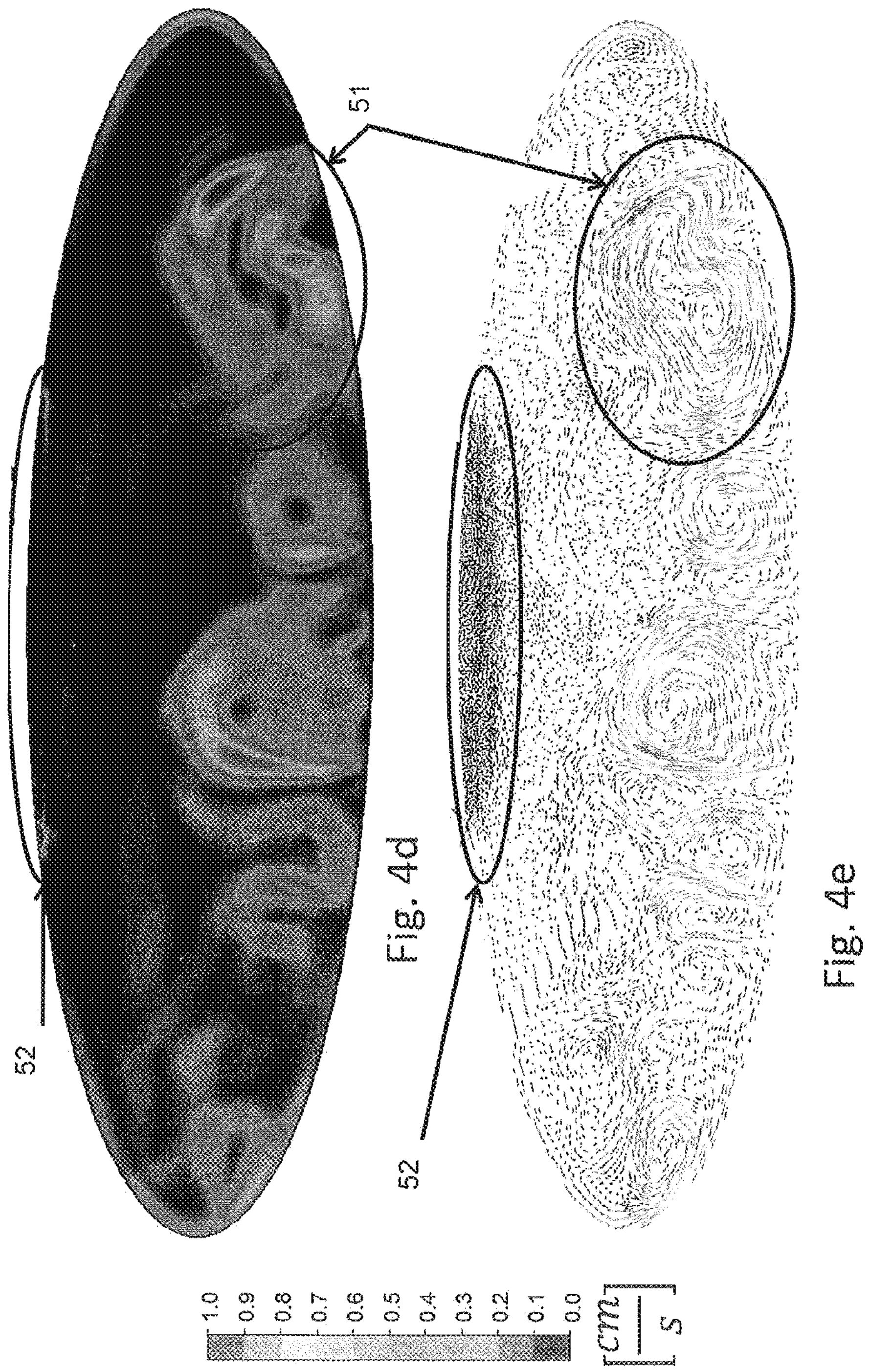
Figure 5:
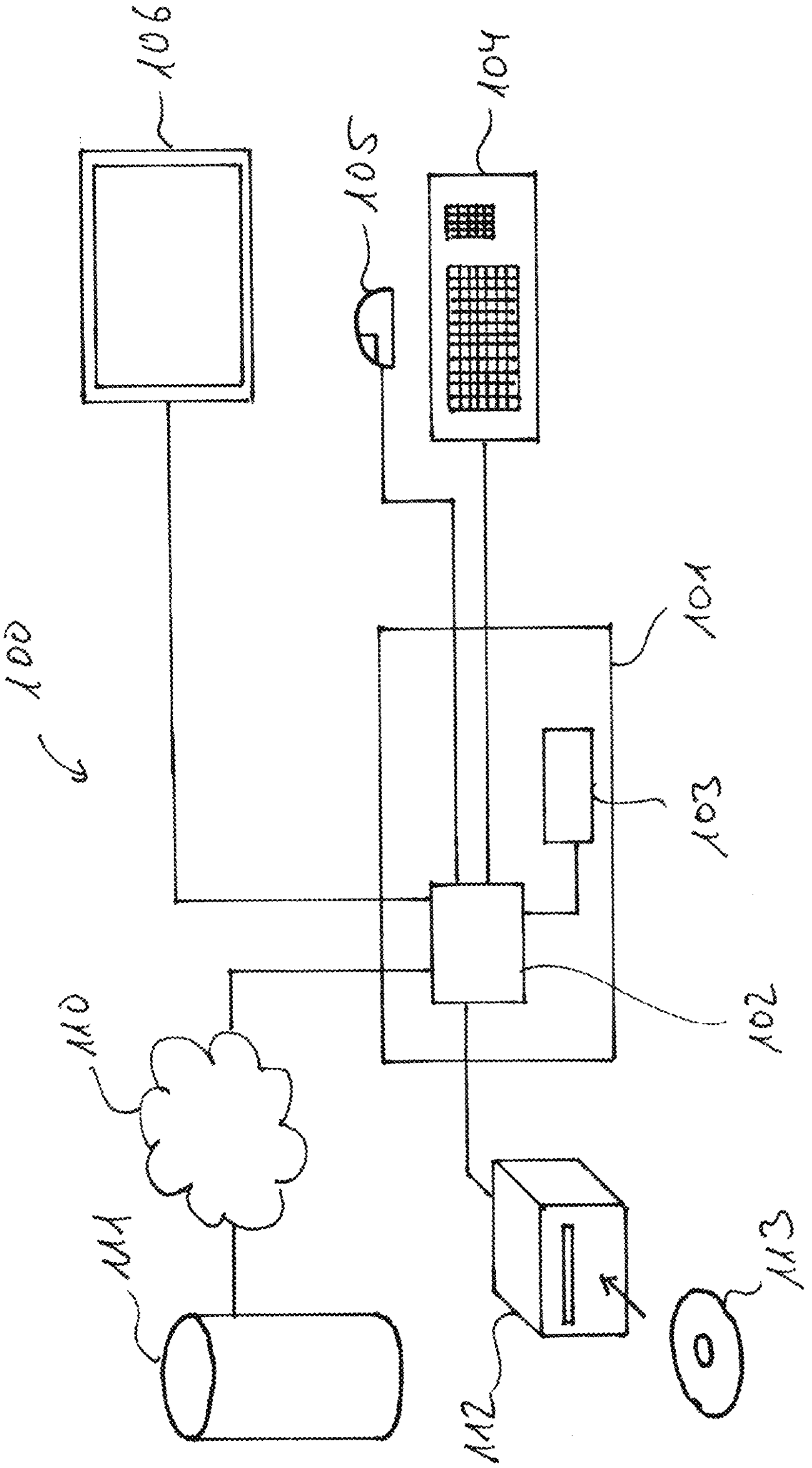

There are shown in:

FIG. 1: a medical device,

FIG. 2: a sterilizer for a medical device,

FIG. 3*a*: a sectional representation of the medical device according to FIG. 1, FIG. 3*b*: a section of FIG. 3*a* with a grid structure, FIG. 4*a*-4*e*: possible visualizations of a simulation result, FIG. 5: a data processing system.

FIG. 1 shows a medical device; in the example represented it is a bag set 1 for peritoneal dialysis.

In peritoneal dialysis, a dialysis fluid is introduced into the patient's peritoneal cavity via a catheter in the abdominal wall. Via the extensive contact of the dialysis fluid with the peritoneum, which surrounds all the organs located in the peritoneal cavity, harmful substances are flushed out of the patient's blood into the dialysis fluid and thus removed from the blood. After a certain dwell time, which as a rule lasts approximately four hours, the dialysis fluid loaded with harmful substances, the so-called dialysate, is drained from the patient's abdomen and replaced by fresh dialysis fluid.

The bag set 1 comprises a solution bag 2, which has two chambers 3, 4 filled with dialysis fluid and a technically required empty chamber 5. Because of its shape, the empty chamber 5 is also referred to as lambda chamber. Each of the chambers 3, 4, 5 is provided with a connection fitting. Two components of a dialysis solution are stored in the chambers 3, 4, a glucose solution and a buffer solution for regulating the pH of the final dialysis solution. The glucose solution and the buffer solution are not mixed until they are used, thus not until immediately before introduction into the patient's peritoneal cavity.

Furthermore, the bag set 1 comprises an empty drainage bag 10, which is provided with two connection fittings. The drainage bag 10 has a single receiving chamber 11 for dialysate, not visible in FIG. 1. To make it easier for the dialysate to run into the drainage bag 10, the latter can be equipped with stiffening rods, not represented.

A central connector 15 of the bag set 1 is used to connect the bag set to the patient's catheter. The central connector 15 is connected to the solution bag 2 and to the drainage bag 10 via tubes 16, 17. Either the solution bag 2 or the drainage bag 10 can be connected to the catheter via a valve, not represented.

The tube 16 connects the central connector 15 to the solution bag 2. In the packaged state, the tube 16 is rolled up in a spiral, therefore it is also referred to as solution coil. At this stage, the tube 16 is connected to the connection fitting of the solution bag 2, which opens into the empty chamber 5. Not until immediately before the use of the bag set 1 is the tube 16 connected to the previously separated chambers 3 and 4 in order to channel the now mixed solutions to the central connector 15.

The tube 17 connects the central connector 15 to one of the connection fittings of the drainage bag 10. A second connection fitting can be provided, for example, in order to gain access to the drainage bag with the aid of a syringe. Then, for example, a test for analysis of the dialysate can be performed. The tube 17 is likewise rolled up in the packaged state and is referred to as a drainage coil.

The individual components of the bag set 1 are subjected to a pre-treatment before being assembled, in order to deposit water in all air-filled spaces for the later sterilization procedure. For this purpose, the components are placed in a vacuum chamber. This chamber is then evacuated to a pressure of, for example, between 150 hpa and 300 hpa residual pressure and then, for example with the aid of a steam nozzle, flooded abruptly with steam, for example to a pressure of approximately 1450 hpa. In the process, the steam penetrates into the cavities of the components of the medical device and condenses to form water droplets. This pre-treatment is referred to as steaming.

The bag set 1 is then assembled and shrink-wrapped in a plastic bag, not represented, for storage and transport.

The pre-packaged bag set 1 must be sterilized before use in order to avoid an infection of the patient. For this purpose, as a rule several bag sets are introduced into a sterilizer, which is represented in FIG. 2.

FIG. 2 shows a sterilizer for medical devices which is an autoclave 20. The autoclave has a sterilization chamber 21, in which in the example represented 24 packaged bag sets 1 are arranged on suitable mesh racks. The sterilization chamber 21 can be sealed in a pressure-tight manner by a door, not represented.

During the sterilization process, the sterilization chamber 21 is charged with superheated steam at high pressure. In the process, a pressure of 2600 hpa and a temperature of approximately 130° C. can be reached, for example.

Due to the combination of high pressure and high temperature, germs present in the bag system 1 are killed, with the result that they can no longer cause an infection of the patient.

The effectiveness of the sterilization process depends on various parameters. In addition to the pressure and the temperature in the sterilization chamber 21 and the treatment duration, these also include the temperatures actually reached in the medical device as well as the quantities of water available in the cavities, the evaporation rate thereof and the resulting steam concentrations.

According to a conventional method for determining the effectiveness of a sterilization process for medical devices, one or more models of the medical device to be sterilized are provided with samples which have a known loading with test germs. As a rule, particularly temperature-stable germs are used as test germs, for example of the species *Geobacillus stearothermophilus.*

The thus-equipped models are then subjected to the sterilization process in question and then the effect of the sterilization process on the samples is determined. For this purpose, they are incubated in a culture solution for several days and the population of the test germs is evaluated.

In order to reduce the effort associated with the conventional method, a method is proposed here for determining the effectiveness of the sterilization process by means of a simulation. For this purpose, the medical device and the interior of the sterilizer are recreated in a three-dimensional grid. This is represented schematically in FIGS. 3*a* and 3*b*.

FIG. 3*a* shows a section through the bag set 1 along a plane which runs through the line A-A' (FIG. 1) and runs perpendicular to the plane of extension of bags 2, 10. It can be seen that the solution bag 2 is formed of a lower film layer 30 and an upper film layer 31, which are joined along joining lines 32, 33, 34, 35 such that the chambers 3, 4 for the dialysis solutions and the lambda chamber 5 are formed.

The drainage bag 10 likewise consists of a lower film layer 40 and an upper film layer 41, which are joined along joining lines 42, 43 such that the receiving chamber 11 is formed.

At the joining lines 32, 33, 34, 35, 42, 43, the respective film layers 30, 31, 40, 41 can be glued, fused, or otherwise joined to each other such that a substantially gas- and liquid-tight join results.

In FIG. 3*b*, an enlargement of a section X from FIG. 3*a* is represented, which represents the lower film layer 30 and the upper film layer 31 of the solution bag 2 in the area of the lambda chamber 5. In addition, a three-dimensional grid 100 is represented here, which serves to recreate the bag set 1 in a data structure.

Although, for reasons of clarity, the grid 100 in FIG. 3*b* is represented two-dimensionally, it is in fact a three-dimensional grid made of a plurality of grid cells Z. In the example represented, all cells Z of the grid are the same size and shape, for example tetrahedrons. Depending on the complexity of the shape of the medical device, some individual cells can also have a different shape and/or size.

For each of the cells Z it is stipulated whether a physical component of the medical device is located at the corresponding point, such as film layers 30, 31 of the solution bag 2 at the locations of cells $Z_1$, $Z_2$, or whether it is a cell in a cavity or in the surroundings of the medical device, such as cells $Z_3$, $Z_4$.

For each cell Z of the grid 100, a data set is provided in the data structure.

For the cells which are filled by physical components of the medical device, the data set contains the prevailing temperature as well as material data of the medical device, such as the elastic properties of the material, the thermal capacity, the thermal conductivity, as well as the permeability to various media (air, water, steam etc.). For the remaining cells, the data set contains the quantities of the media (air, water, steam etc.) present in the respective cell as well as data on their thermodynamic state (temperature, pressure, flow rate and direction etc.). In addition, for each cell representing a cavity, information is provided regarding a germ load or a reduction in the germ load achieved.

Between adjacent cells Z, boundary surfaces G are formed, which are recognizable in FIG. 3*b* as lines. The data structure can additionally comprise data sets for boundary surfaces. These data sets primarily comprise information about whether the boundary surface is a physical surface, for example an inner or outer surface of a medical device, and optionally a germ loading of the surface or a reduction in this germ loading already achieved.

The data structure is then filled with data such that it represents an initial state at the start of the sterilization process. For example, approximately room temperature will be present in all cells and the pressure is approximately 1000 hpa in each cell which represents a cavity.

At the same time, in all cells which are located outside the medical device, a mixture of air and steam will be present, for example steam or steam-air mixture at approx. 2.6 to 3.6 bar absolute pressure and a temperature of for example 130° C.

In the case of cells which are located in sealed cavities of the medical device, the previous steaming can yield other relationships. Thus, some cells here may be filled with water whereas in other cells there is a mixture of air and steam and also condensed water, which corresponds to a complete saturation.

For cells in liquid-filled cavities of the medical device, all cells are correspondingly filled with the respective liquid.

Subsequently, it is computationally determined step by step how the relationships in the individual cells Z of the grid change while the sterilization process is being carried out. In the process, a time interval recreated by a computation step can be one second, for example, but longer or shorter time intervals can also be implemented.

During a heating phase of the sterilization process, superheated steam is fed to the sterilization chamber 21, with the result that in some cells, which represent this space, pressure, quantity of steam and temperature increase. As soon as differences exist between two adjacent cells, a transfer of energy and/or media through the respective boundary surface between the cells takes place. The resulting changes of state of the individual cells are determined computationally. The computation methods to be used for this are sufficiently known from computational fluid dynamics and therefore do not need to be explained in more detail here. Essentially, the following effects are to be taken into consideration here:

Temperature equalization: if a difference in temperature exists between two adjacent cells, thermal energy is transferred through the boundary surface from the warmer to the colder cell, whereby the temperatures align.

Pressure equalization: if a difference in pressure exists between two adjacent cells, some of the media will flow out of the cell at higher pressure through the boundary surface into the cell at lower pressure, with the result that the pressures align.

Concentration equalization: if a difference in concentration of a medium, or a difference in the partial pressures of the media, exists between two adjacent cells, some of the medium will diffuse through the boundary surface into the cell at lower concentration or partial pressure, with the result that the concentrations or partial pressures align.

Gravity: if a difference in altitude exists between two cells, some of the media will flow out of the higher-placed cell through the boundary surface into the lower cell.

Natural convection: if a difference in density exists between two adjacent cells, this results in natural convection.

The interaction of pressure equalization, gravity, convection and concentration equalization (diffusion) leads to a height-dependent change in the mixing ratio of gaseous media such as air, steam and ethylene oxide. This can have effects on the effectiveness of the sterilization process and therefore has to be recreated computationally as precisely as possible.

Convection processes have a significant influence on the temperature distribution in particular in liquid-filled parts of medical devices. For this reason too, as precise as possible a reproduction of such convection processes is necessary. In addition, convection processes are decisively involved in the distribution of media, such as steam for example, into parts of the medical device which do not contain, or do not contain sufficient quantities of, the relevant medium at the start of the sterilization process. This applies, for example, to the penetration of steam into the tubes 16, 17 and into the central connector 15.

After completion of the heating phase, the state of the atmosphere in the sterilization chamber 21 is kept constant, with the result that substantially only equalization processes still take place within the medical device. However, the profile of these equalization processes is of considerable importance for the success of the sterilization process, therefore the entire duration of the sterilization process is further recreated or simulated according to the method described above.

A cooling process, in which above all the dialysis solutions present in the solution bag are to be cooled in order to prevent premature degradation, following the sterilization process can on the other hand optionally be omitted.

Further media can be taken into consideration in the simulation. Thus, for example, a biocidal gas such as ethylene oxide can be introduced into the sterilization chamber and diffuse into the medical device. The corresponding diffusion processes can be recreated by the simulation process. For example, the injection of ethanol, into plug-in connectors for example, can also be reconstructed in this way.

The diffusion of media through the material of the medical device can be modelled in the simulation by adding to the data structure data on the absorbing capacity (for example as permeability or diffusion data) of the material for individual media. If, for example, the material can absorb a certain quantity of steam, then steam will diffuse into the respective cell via a boundary surface if the concentration of the steam in the adjacent cell is high enough. In this way, steam can spread slowly through the material cell by cell and also escape again at boundary surfaces to cavities where there is a lower concentration. Thus, for example, steam can diffuse from the sterilization chamber through the film layers 30, 31 into the lambda chamber 5. The diffusion of other media such as ethylene oxide or ethanol can also be simulated in the same way.

During the sterilization process, further effects can occur, which need to be taken into consideration in the simulation. Thus, for example, in sealed volumes of a medical device an increase in the internal pressure will result. This increase in pressure is particularly relevant when liquid water, which evaporates due to the increase in temperature, is present in the corresponding volumes at the start of the sterilization process. The evaporation process needs to be taken into consideration in the simulation since it has a significant influence on the distribution of heat in the medical device. Likewise, condensation can occur at some points of the medical device, which likewise influences the temperature distribution.

As a result of the evaporation of water, the lambda chamber 5 or the receiving chamber 11 can also swell, whereby the geometry of the corresponding volumes changes.

Account can be taken of this effect in different ways. For one thing, the elastic and/or plastic deformability of the material of the medical device can be stored in the data structure. Then, in each computation step it can be determined whether a force is acting on a cell which represents a physical component of the medical device so that it moves. If a movement of the material in the cell is detected, either the grid can remain unchanged and the movement can be depicted by allocating the corresponding state data to an adjacent cell into which the material has moved. It can also become necessary for individual cells to have to be added or removed. However, this can have the result that, after the displacement, cells exist which are no longer assigned any state data, which leads to problems.

A better solution is to construct the entire grid dynamically in such a way that the size and position of the individual grid cells can change in order to take account of such expansion effects. Care is to be taken here that, in areas in which a significant change in volume is to be expected, a sufficiently fine grid structure is chosen so that the result does not become imprecise due to grid cells ultimately being too large.

As a decisive part of the simulation, in each computation step the effect of the state prevailing in each case on a possible germ population is calculated for each cell of the grid which does not correspond to a physical component of the medical device, and for each boundary surface which represents a physical surface. During the stipulation of the initial state, each cell or boundary surface can be assigned a particular germ loading, for example an occupancy with $10^6$ germs of the species *Geobacillus stearothermophilus*.

Figure 6A:
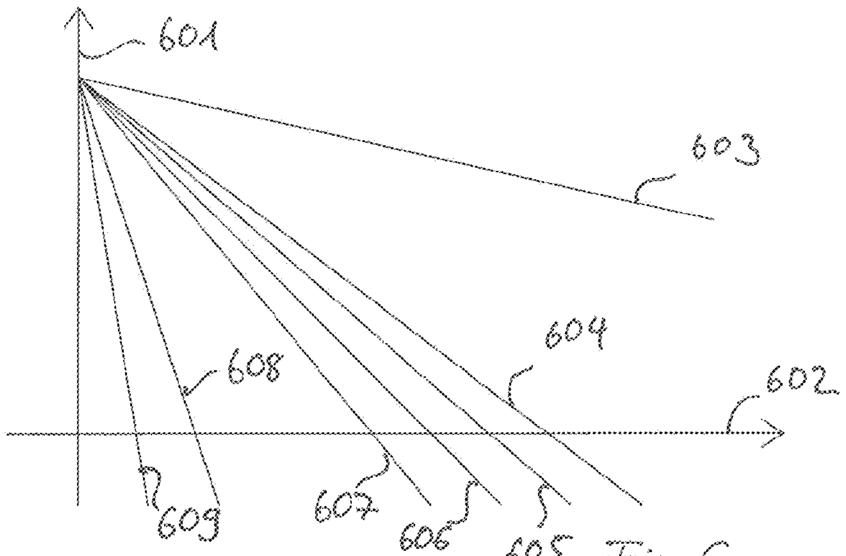
Figure 6B:
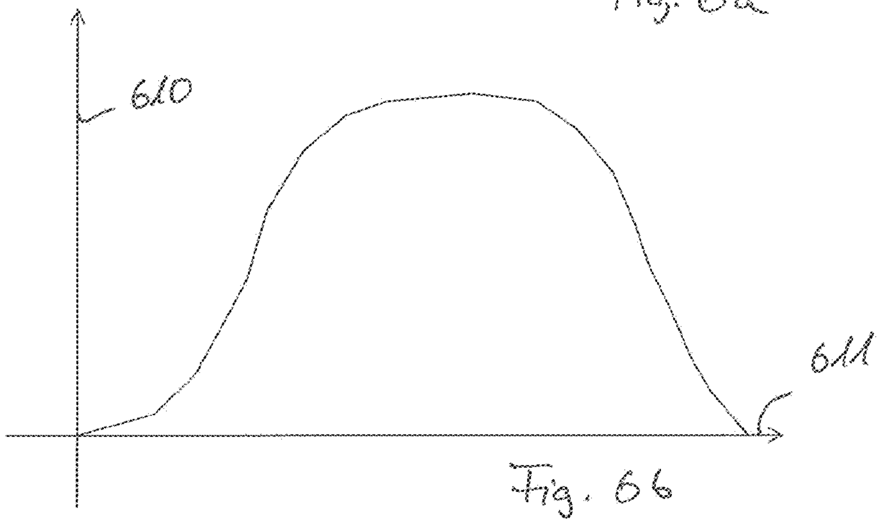
Figure 6C:
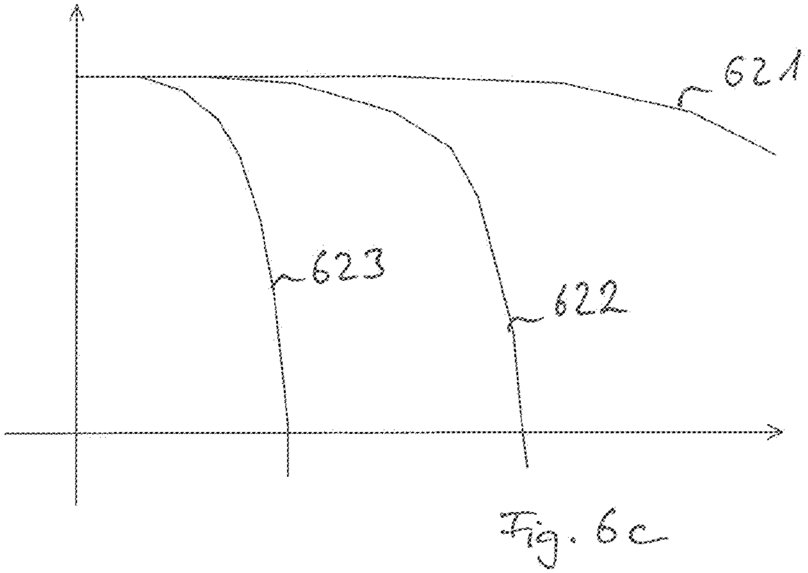

The relationship between the temporal profile of a germ loading, the temperature and an atmospheric composition is represented in FIGS. 6*a* to 6*c*.

FIG. 6*a* shows the profile of the germ loading in a cell or boundary surface of the grid at a constant temperature and with various atmospheric compositions. The germ load log(N) is plotted on the vertical axis 601 in random logarithmic units, while the time is plotted on the horizontal axis 602. The intersection of the axes represents on the one hand a non-hazardous germ loading (e.g. log(N)=−6) and on the other hand the start of the sterilizing process (e.g. t=0).

The diagonal lines 603, 604, 605, 606, 607, 608, 609 represent the temporal profile of the germ loading in the case of various atmospheric compositions. Thus, the line 603 shows a very slow reduction in a pure air atmosphere, the lines 604, 605, 606 show the quicker reduction in an air-steam mixture (604: 80% air, 605: 50% air, 606: 20% air), the line 607 shows the reduction in a pure steam atmosphere. The lines 608, 609 represent the reduction of the germ loads in pure water (line 608) and in dialysis solution (line 609).

The gradients of the lines 603 to 609 represent in each case the inactivation rate k which ensues in the atmosphere in question.

An example of a temperature profile which ensues in a cell of the grid during a sterilization procedure is represented in FIG. 6*b*. Here, the temperature is represented on the vertical axis 610 in random units, while the time is represented on the horizontal axis 611 again. It can be seen that during the sterilization procedure the temperature first of all rises to a maximum, in order then to fall again.

Finally, in FIG. 6*c* profiles of germ loadings are represented which result taking into consideration the atmospheric composition and the temperature profile according to FIG. 6*b*. Here, for better clarity, only three profiles 621, 622,

623 are represented, which correspond to the atmospheric compositions of the lines 601, 606, 609.

With the aid of the finite difference equation $\Delta N_i = -k_i * N_i * \Delta t$, the change in the germ loading and the remaining germ loading are now determined. Here, the inactivation rate k is determined in dependence on the respectively present ambient parameters, thus the temperature, the steam concentration and/or the concentration of active media such as ethylene oxide, for example. This likewise applies to volume inactivation rates $k_V$ and to surface inactivation rates $k_O$.

Instead of the calculation of a notional germ loading, in each computation step and for each computation cell a logarithmic germ reduction F can also be determined and then added up, in order to determine the germ reduction achieved during the entire sterilization process:

$$F_i = \log\frac{N_{i+1}}{N_i} = \log(1 - k_i * \Delta t)$$

$$F_{tot} = \log\frac{N_{end}}{N_{start}} = \sum F_i$$

The results of the simulation can be represented or visualized in different ways. One possibility is to output the smallest germ reduction achieved in the medical device as a number.

The profile of a parameter of interest over the duration of the sterilization process can be output as a graph for a selected cell.

Further possibilities are to represent selected parameters colour-coded or greyscale-coded in sectional representations of the medical device. In the process, the state at a particular point in time during the sterilization process can be represented, for example the temperature or the germ reduction achieved after 1000 seconds, after 2000 seconds and at the end of the sterilization process.

In FIGS. 4*a* to 4*c*, visualizations of the temperature of the dialysis solutions after a sterilization process are represented, for example. FIG. 4*a* shows the temperature at the outer surfaces of the solution chambers 3, 4, FIG. 4*b* shows the temperature in a section parallel to the surface of extension of the solution bag 2, and FIG. 4*c* shows the temperature in a section perpendicular thereto. It can be seen that a very homogeneous end temperature of the solutions has been achieved in the example represented.

The flow rates in the medical device prevailing at a particular point in time can be visualized in the same way. Thus, for example, FIGS. 4*d* and 4*e* show the flow conditions in a solution bag after approximately 1000 seconds, wherein FIG. 4*d* represents a contour plot with greyscale-coded rates, while FIG. 4*e* shows a vector representation of the flow directions. Here, convection vortices 51 can be clearly seen in a liquid-filled part of the bag, while hardly any flow prevails in a small air bubble 52 in the upper area of the figures.

The profile of the respective parameters over the duration of the sterilization process can also be provided as a video. In similar representations, pressure, steam concentration and/or germ reduction achieved can also be represented.

The described simulation process can be utilized in order to determine the effectiveness of a sterilization process for a particular medical device, such as for the bag set 1 in the example represented. In this way, e.g. after a design change or redevelopment of a medical device, it can be checked whether a known sterilizing process is adequate for reliably sterilizing the medical device. In this way, the effects of adaptations on the sterilizability can be tested without having to manufacture and sterilize sample copies for every adaptation.

New or altered medical devices can thus be brought to market quickly since the effectiveness of a suitable sterilization process can be proven quickly.

In the same way, parameter changes in sterilization processes can be tested with the described simulation process for their effects on the result, without having to accept the described effort for implementation and sampling.

In order to test individual components of a medical device with respect to their sterilizability, it can make sense to restrict the simulation initially to these components and their immediate surroundings. The computational effort required can thereby be significantly reduced. However, a full simulation should always be effected for a conclusive assessment.

Finally, it is even conceivable to utilize the results of the described simulation process to validate a sterilization process for the regulatory approval of a new or altered medical device or of a sterilization process.

For this purpose, a germ reduction to be achieved by the sterilization process is predetermined, which is for example a 12-log reduction, thus a germ reduction by a factor of $10^{12}$. Then, the simulation is used to check that the required germ reduction is achieved at every point of the medical device. If the required reduction is achieved, the successful sterilization is validated and the medical device can be approved.

The reliability of the proof can be further increased if sampling with a sample is effected in addition to the simulation and the result of the simulation is compared with the result of the sampling. The approval can then be made dependent on the results matching.

In contrast to the conventional validation process, here the sampling can be effected at a point of the medical device which is not a critical point, since only the match with the simulation result needs to be proved. The effort of the sampling can hereby be reduced. Influences of the sample on the media distribution in the medical device can be taken into consideration in the simulation or compensated for by a corresponding addition or deduction of media.

In contrast to the conventional validation process, proving the match between simulation and sampling can optionally be effected in an interrupted sterilization process, if for example the germ reduction actually necessary has not yet been achieved. This has the advantage that a larger population of test germs, which can be evaluated more easily, is still present on the sample after the sterilization process.

By means of the described validation process, a new or altered medical device can be brought to market even more quickly.

In the simulation process described it must be taken into consideration that the initial state is possibly not identical for every individual medical device. Thus, in particular the position and/or size of water droplets which enter the medical device as a result of the steaming can be random and can differ from medical device to medical device. Precisely in the case of medical devices with awkward geometries, for example long tube sections, the position of water droplets in the tube section can have relevant effects on the result of the sterilization process.

It can therefore be necessary to model some possible distributions of the water droplets and to simulate the effects separately. A validation would then have to be based on the distribution which gives the worst sterilization result.

In order to determine the effect of the steaming of the medical device and a distribution of water droplets in the medical device resulting therefrom, a simulation process designed analogously to the above-described simulation process of the sterilization process can also be carried out for the steaming process. However, it must be taken into consideration here that the actual position and size of water droplets forming through condensation are, for one thing, greatly influenced by chance, with the result that at best estimates are possible. For another thing, the water droplets can move and combine in the medical device when the medical device is moved between the steaming and the sterilization.

The described simulation process can be carried out on a data processing system, such as is represented in FIG. 5.

The data processing system 100 comprises a central processing unit 101 with at least one processor 102 and a storage element 103. The at least one processor 102 can be a powerful multi-core processor which is optimized for executing complex mathematical tasks. The storage element 103 can comprise writable components (RAM) and read-only components (ROM). The storage element 103 preferably has a large storage capacity and a high read/write speed.

The central processing unit 101 can be formed by a commercially available computer, e.g. a PC.

The central processing unit is connected to input means and output means, via which information about the sterilization process to be simulated can be input and output. The input means can comprise e.g. a keyboard 104 and a mouse 105. The output means can comprise a monitor 106. If the monitor 106 is a touchscreen, this can also function simultaneously as input means.

The central processing unit can be connected to a database 111, in which design data of one or more medical devices, one or more sterilizers and/or data for one or more sterilization processes are stored, directly or via a network 110. The processor 102 can access the data stored in the database 111 in order to recreate a medical device and/or a sterilizer in a data structure, and/or in order to recreate a sterilization process by means of the simulation process described above.

The central processing unit 101 is furthermore connected to a read/write device 112 for data carrier 113. In the example represented, the data carrier 113 is a CD or DVD, alternatively other known removable or non-removable data carriers can also be used.

Program code information, which can be transferred to the storage element 103 by the processor 102, can be saved on the data carrier 113. The processor 102 can then read and execute this program code information from the storage element 103 in steps, whereby the processor is prompted to execute the simulation process described above.

The central processing unit can likewise utilize the read/write device to save results of the simulation process on a data carrier 113. Alternatively, the results can be visualized on the monitor 106 and/or stored in the database 111.

For better clarity, the representation of the data processing system 100 in FIG. 5 is greatly simplified. In particular, in a real data processing system the at least one processor 102 will not be connected to the peripheral devices 104, 105, 106, 112 directly, but via suitable interface elements.

The invention claimed is:

1. A process for determining the effectiveness of a sterilization process for a medical device in a sterilizer, the process being carried out by execution of a program code by a processor, the process comprising steps of providing a data structure, wherein the data structure represents a fine grid formed of a plurality of three-dimensional cells, recreating the medical device arranged in the sterilizer as a three-dimensional model in the data structure in such a way that a first multiplicity of cells of the fine grid represent a body of the medical device and that a second multiplicity of cells of the fine grid represent an interior of the sterilizer which is not occupied by the body of the medical device, recreating an initial state in the data structure in such a way that each cell of the second multiplicity of cells is assigned data relating to a temperature prevailing at the location of the cell, a quantity of a first medium located in the area of the cell and a quantity of a second medium located in the area of the cell, recreating the sterilization process by entering information about the sterilization process to the data structure, the recreating comprising step by step intervals of changes in the temperature, in the quantity of the first medium, and in the quantity of the second medium occurring in each cell of the second multiplicity of cells during the sterilization process, calculating a reduction in a germ loading achieved in each cell of the second multiplicity of cells during the sterilization process taking into consideration the prevailing temperature, the quantity of the first medium, and the quantity of the second medium in the respective cell in each of the step by step intervals, determining the effectiveness of the sterilization process based on the calculating, and sterilizing the medical device by subjecting the medical device to the sterilization process that is determined as effective.

2. The process according to claim 1, wherein each cell of the second multiplicity of cells is further assigned a quantity of a third medium, the recreating further comprises step by step intervals of changes in the quantity of the third medium, and the calculating further comprises taking into consideration the quantity of the third medium in the respective cell in each of the step by step intervals.

3. The process according to claim 2, wherein a phase transition of the first, second and/or third medium is taken into consideration for the recreating of the sterilization process.

4. The process according to claim 2, wherein a diffusion of the first, second and/or third medium through the material of the medical device is taken into consideration for the recreating of the sterilization process.

5. The process according to claim 2, wherein a convection of the first, second and/or third medium between the cells of the second multiplicity of cells is taken into consideration for the recreating of the sterilization process.

6. The process according to claim 2, wherein the second or the third medium is ethylene oxide.

7. The process according to claim 1, wherein the calculation of the reduction in the germ loading is made taking into consideration a volume inactivation rate $k_V$, which is dependent on the composition of an atmosphere prevailing in the respective cell.

8. The process according to claim 1, wherein, for each boundary surface between a cell of the first multiplicity of cells and a cell of the second multiplicity of cells, the reduction in a germ loading on the corresponding boundary surface is calculated, wherein for the calculation a surface inactivation rate $k_O$ results, which is dependent on the composition of the atmosphere prevailing in an adjacent cell of the second multiplicity of cells and on the material of which the boundary surface consists.

9. The process according to claim 1, wherein a shape change of the medical device is taken into consideration for the recreating of the sterilization process.

10. The process according to claim 1, wherein the first medium is air.

11. The process according to claim 1, wherein the second medium is water.

12. A process for validating a sterilization process for a medical device with the following steps:

stipulating a required reduction in a germ loading to be achieved by the sterilizing process;

carrying out the process according to claim 1, comparing the reduction in the germ loading determined in each cell of the second multiplicity of cells; and classifying the sterilization process as effective if the required reduction in the germ loading has been achieved for each cell of the second multiplicity of cells, or classifying the sterilization process as not effective if the required reduction in the germ loading has not been achieved for at least one cell of the second multiplicity of cells.

13. The process according to claim 12, wherein a control procedure with the following steps is additionally carried out:

introducing a sample provided with a known germ loading at a predetermined point of a medical device to be sterilized, carrying out the sterilization process to be validated with the medical device, determining the reduction in the germ loading of the sample achieved by the sterilization process, and only classifying the sterilization process as effective when the reduction in the germ loading of the sample actually achieved corresponds sufficiently precisely to the reduction in the germ loading calculated for the corresponding point.

* * * * *